United States Patent [19]
Mörsdorf et al.

[11] Patent Number: 6,140,334
[45] Date of Patent: Oct. 31, 2000

[54] POLYMORPHIC FORM OF DOXAZOSIN MESYLATE (FORM III)

[75] Inventors: Johann Peter Mörsdorf, Langenzenn; Ingomar Grafe, Nürnberg, both of Germany

[73] Assignee: Heumann Pharma GmbH, Nurnberg, Germany

[21] Appl. No.: 08/992,251

[22] Filed: Dec. 17, 1997

[30] Foreign Application Priority Data

Dec. 20, 1996 [EP] European Pat. Off. ............ 96 120 603

[51] Int. Cl.$^7$ ...................... C07D 403/14; A61K 31/517
[52] U.S. Cl. .......................................... 514/260; 544/291
[58] Field of Search .............................. 544/291; 514/260

[56] References Cited

U.S. PATENT DOCUMENTS

| | | | |
|---|---|---|---|
| 2,699,054 | 1/1955 | Conover | 260/559 |
| 4,092,315 | 5/1978 | Bianco | 544/291 |
| 4,188,390 | 2/1980 | Campbell | 424/251 |
| 4,251,532 | 2/1981 | Roteman | 424/251 |
| 4,816,455 | 3/1989 | Schickaneder et al. | 514/254 |
| 5,294,615 | 3/1994 | Meyer et al. | 514/254 |
| 5,412,095 | 5/1995 | Morley et al. | 544/291 |
| 5,504,207 | 4/1996 | Mannino et al. | 544/291 |

FOREIGN PATENT DOCUMENTS

| | | |
|---|---|---|
| 0459666 | 12/1991 | European Pat. Off. . |
| 94/09783 | 5/1994 | WIPO . |

OTHER PUBLICATIONS

Xu Liying et al, *Chinese Journal of Medicinal Chemistry*, vol. 5, No. 4, p. 266 (1995).

The Merck Index, 1996, Merck & Co., Inc., Whitehouse Station, N.J., XP002030968, #3489: Doxazosin.

*Primary Examiner*—John M. Ford
*Attorney, Agent, or Firm*—Burns, Doane, Swecker & Mathis, L.L.P.

[57] ABSTRACT

A new crystalline and anhydrous form of doxazosin mesylate is described. The new form is crystalline and anhydrous and is characterized in its X-ray spectrum by the following reflex positions of high and medium intensity: 8.49°, 11.72°, 16.03°, 18.29°, 21.03°, 22.87° and 25.02°. Owing to its crystalline properties, the new form of doxazosin mesylate according to the invention has surprising advantages both with regard to its synthesis and for pharmaceutical processing into solid dosage forms. A process for preparing the new form of doxazosin mesylate and pharmaceutical compositions comprising the new form of doxazosin mesylate are also described.

21 Claims, 2 Drawing Sheets

X-Ray Diffraction Pattern of Form III of Doxazosin Mesylate according to the Invention DTA Spectrum of Form III of Doxazosin Mesylate according to the Invention

POLYMORPHIC FORM OF DOXAZOSIN MESYLATE (FORM III)

CROSS-REFERENCE TO COMPANION APPLICATIONS

Copending applications Ser. No. 08/992,474 [Attorney Docket No. 015200-048] and Ser. No. 08/992,252 [Attorney Docket No. 015200-049], filed concurrently herewith and assigned to the Assignee hereof.

BACKGROUND OF THE INVENTION

1. Technical Field of the Invention

This invention relates to a new crystalline and anhydrous form of doxazosin mesylate, a process for its preparation and pharmaceutical compositions comprising this new Form III.

2. Description of the Prior Art 1-(4-Amino-6,7-dimethoxy-2-quinazolinyl)-4-[(2,3-dihydro-1,4-benzodioxin-2-yl)carbonyl]piperazine methanesulfonate, the INN name of which is doxazosin mesylate, is a diaminoquinazolyl derivative of the class of the $\alpha_1$-receptor blockers and has the structural formula.

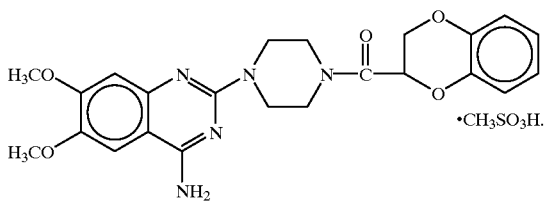

It shows a great structural similarity to the older representatives of this class, prazosin hydrochloride and terazosin hydrochloride. Whereas the two latter active substances are used primarily only in the treatment of high blood pressure, in the case of doxazosin mesylate, there is an additional indication, namely, the treatment of benign prostate hyperplasia.

Unlike prazosin and terazosin, doxazosin is used therapeutically not as the hydrochloride but as the mesylate, that is, as a salt of methanesulfonic acid.

Although medicaments containing doxazosin mesylate are already on the market, doxazosin mesylate has not hitherto been described. Even U.S. Pat. No. 4,188,390, which discloses doxazosin for the first time, does not contain a description of doxazosin mesylate. Only doxazosin monohydrochloride is described in the examples in that publication.

Because of its extremely sparing solubility in water, however, the hydrochloride is unsuitable for pharmaceutical purposes.

Attempts to prepare doxazosin mesylate in the conventional ways prove to be very difficult and lead to unsatisfactory results. On the one hand, doxazosin base is sparingly soluble in the solvents commonly used for forming salts. It is sufficiently soluble only in polar, aprotic, high-boiling solvents such as, for example, dimethylformamide. In these solvents, however, the solubility of doxazosin mesylate is similar to that of the base, so that the yields of mesylate obtained are totally unsatisfactory. Moreover, from the pharmacological aspect, dimethylformamide is a critical residual solvent in medicinally active substances. The current ICH guideline for residual solvents in pharmaceutical active substances ("ICH Guideline: Residual Solvents," *Pharmeuropa,* Vol. 8, No. 1, page 103, March 1996) places dimethylformamide in Class 2 as a solvent having known toxicity and limits the permissible residual content of the solvent to 500 ppm.

On the other hand, a second standard method for forming salts also fails because of the particular properties of doxazosin base and its salts. Doxazosin base can be dissolved in weak acids such as, for example, acetic acid, and in this phase can be subjected to clarification filtration for the removal of insoluble foreign particles which is indispensable for a pharmaceutical active substance, and afterwards the mesylate can be precipitated by adding methanesulfonic acid or a salt of methanesulfonic acid. When this procedure is carried out at room temperature, however, an unfilterable gel is obtained. If the procedure is carried out at more elevated temperatures, for example 50° C., this gel agglomerates or, in higher concentrations, separates out as a second, non-solidifying oily phase. Through the addition of organic solvents such as, for example, acetone, the suction capacity of the precipitated doxazosin mesylate can be improved. However, drying of this product leads to the formation of lumps owing to the high moisture content, and impurities from the mother liquor, in particular coloring impurities, are included therein. Ultimately, a form of doxazosin mesylate is obtained which is shown by the X-ray spectrum to be amorphous and is moreover hygroscopic. Thermal analysis reveals an exothermic transformation at 200° C. before the substance melts with decomposition at 267° C.

SUMMARY OF THE INVENTION

This invention is therefore based on the object of providing a crystalline and anhydrous form of doxazosin mesylate which, owing to its physical properties, in particular its crystalline properties and its behavior in water, is easy to handle both during its chemical preparation and during pharmaceutical formulation.

This object is fulfilled according to the invention by a new crystalline and anhydrous form of doxazosin mesylate, which is referred to below as Form III.

This invention accordingly provides Form III of doxazosin mesylate, which shows an X-ray powder diagram having the following reflex positions of high and medium intensity: 8.49°, 11.72°, 16.03°, 18.29°, 21.03°, 22.87° and 25.02°, and which is crystalline and anhydrous.

DETAILED DESCRIPTION OF BEST MODE AND SPECIFIC/PREFERRED EMBODIMENTS OF THE INVENTION

Figure 1:
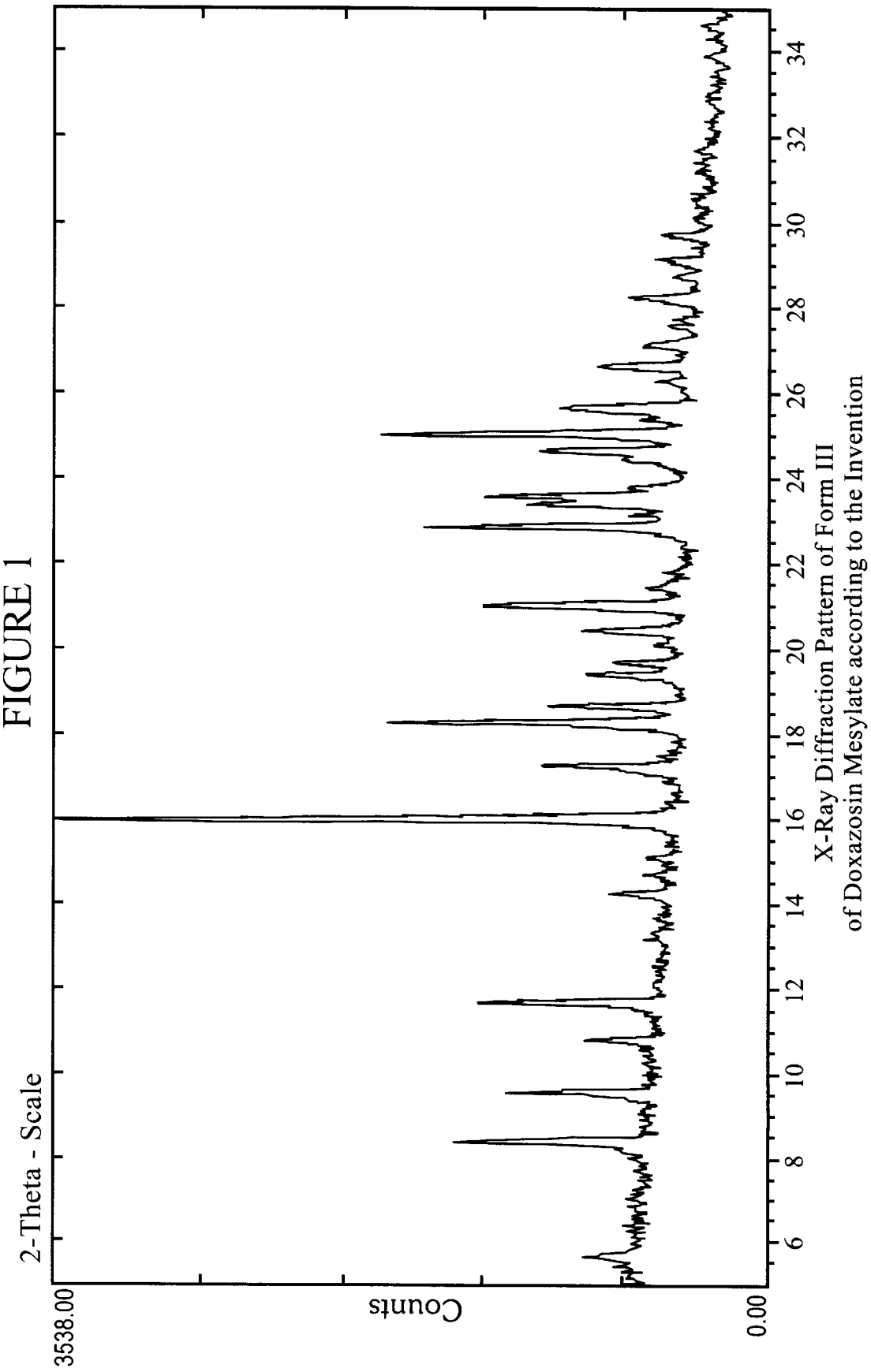
FIG. 1 is an X-ray diffraction pattern of Form III doxazosin mesylate in accord with the invention.

Form III according to the invention has the characteristic X-ray diffraction pattern as shown in FIG. 1, measured with the use of Cu—$K_{\alpha 1}$ radiation and of a Ge monochromator having a spacing of 0.017° within the diffraction angle range 2 θ of 50 to 35°, and reflex positions of high and medium intensity at 8.49°, 11.72°, 16.03°, 18.29°, 21.03°, 22.87° and 25.02°.

Form III of doxazosin mesylate according to the invention differs from the other forms of doxazosin mesylate in a number of other properties over and above the X-ray diffraction pattern. These properties can therefore also be used to distinguish it from the other forms.

Figure 2:
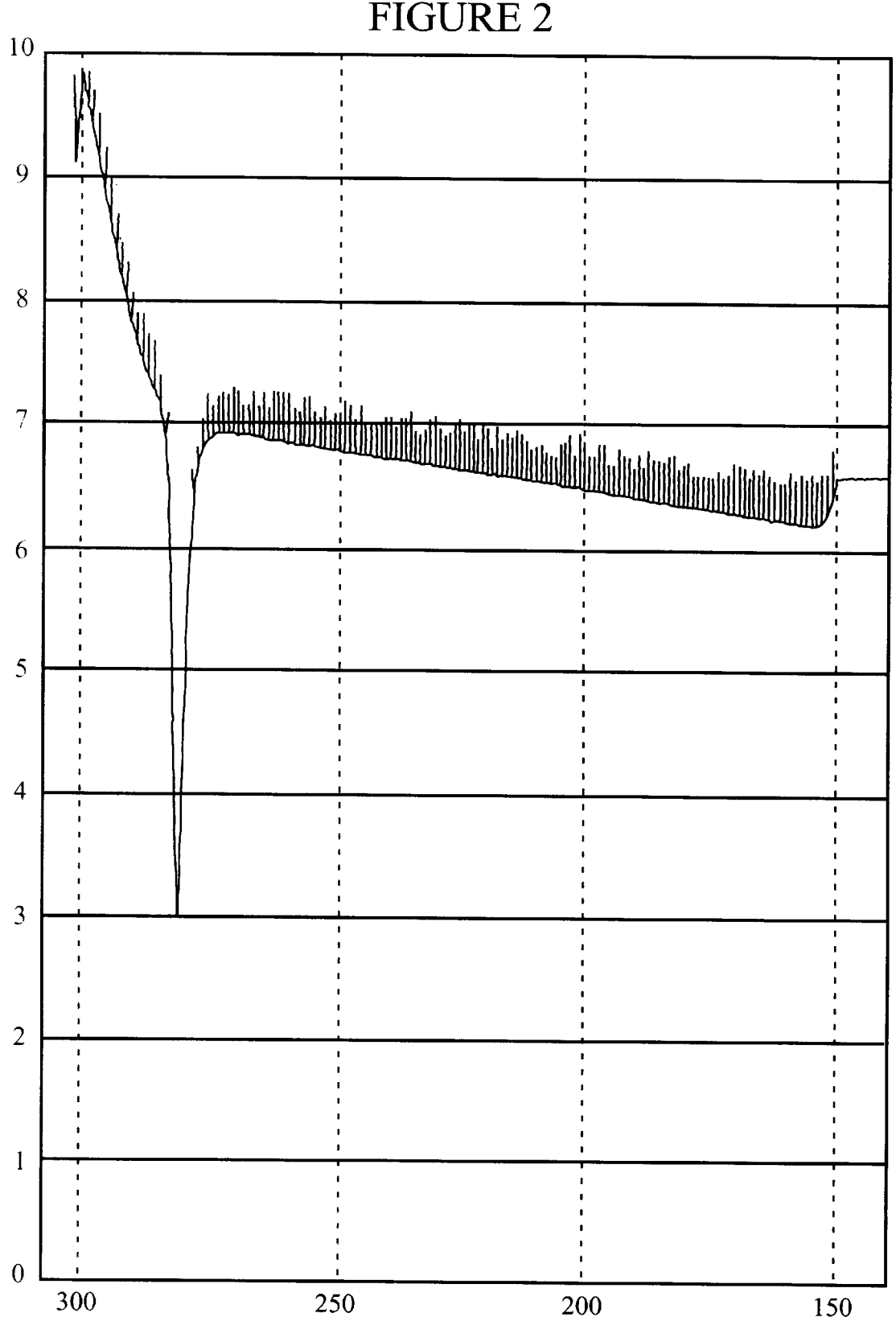
FIG. 2 is a DTA spectrum of Form III doxazosin mesylate in accord with the invention.

Form III of doxazosin mesylate can be further characterized with the aid of differential thermal analysis (DTA). From the DTA spectrum of Form III measured in the range of 150° C. to 300° C., which is shown in FIG. 2, Form III has a characteristic single endothermic peak at 281°C., which corresponds to the melting point of Form III.

The invention also provides a process for preparing the above Form III of doxazosin mesylate according to the invention, which comprises:

(1) reacting doxazosin base with acetic acid to afford doxazosin acetate, optionally in an organic solvent;

(2) clarifying the solution obtained in step (1) in the hot state and mixing it with methanesulfonic acid;

(3) stirring the solution obtained in step (2) at a temperature of from about 30°C. up to the reflux temperature of the solvent to achieve substantially complete crystallization, and recovering the solvent adduct thus obtained by filtration;

(4) introducing the moist solvent adduct into a lower alcohol and boiling at the reflux temperature for between about 10 minutes and about 12 hours; and (5) cooling the solution obtained in step (4) to room temperature and recovering the crystals which precipitate by filtration.

In the first step of the process according to the invention, doxazosin base is converted with acetic acid into doxazosin acetate. Conversion may be effected in the absence of a solvent or, preferably, in an organic solvent. Examples of suitable solvents are lower alkyl alcohols or esters, an ester solvent such as ethyl acetate being preferred. In the course of the reaction, the ratio of doxazosin base to acetic acid advantageously amounts to between about 1:2 and about 1:5, preferably between about 1:2 and about 1:3. The reaction temperature typically amounts to between about 40° C. and about 100° C., preferably between about 60° C. and about 90° C., in particular about 80° C. In the individual case, it depends on the composition of the reaction mixture.

The solution obtained in the first step is clarified when still in the hot state and is mixed with methanesulfonic acid. After washing the filter layer with a hot mixture of glacial acetic acid and an organic solvent, preferably the same solvent as used in stage (1), while the volumetric ratio preferably amounts to about 1:1, the filtrate and the washing liquid are combined and mixed with methanesulfonic acid. The methanesulfonic acid is advantageously employed in an approximately equimolar quantity relative to the doxazosin acetate or in a slight excess of up to about 10 mol %, preferably up to about 7 mol %. The addition of an approximately equimolar quantity of methanesulfonic acid is preferred. The methanesulfonic acid is preferably employed in the form of a 70% aqueous solution.

In the fourth stage of the process according to the invention, the solvent adduct that is still moist with solvent is introduced into a lower alkyl alcohol such as methanol or ethanol, preferably methanol, and refluxed for between about 10 minutes and about 12 hours, preferably for from about 6 to about 9 hours. The lower alkyl alcohol is generally employed in this connection in a quantity amounting to between about 1:5 and about 1:20 relative to the moist solvent adduct.

In the last step, the solution obtained as described above is cooled to room temperature until the desired compound has fully precipitated in the form of crystals. The precipitated crystals are recovered by filtration as usual.

Owing to its crystalline properties, Form III of doxazosin mesylate according to the invention has surprising advantages both with regard to its synthesis and the purity of the product and for its pharmaceutical processing into solid dosage forms. As described above, the forms of doxazosin mesylate prepared in the conventional ways are obtained in the form of gel-like precipitates which even in the presence of organic solvents are very voluminous, contain large quantities of mother liquor and therefore have moisture contents and drying losses respectively of up to 50%. Because of this, impurities, in particular coloring impurities, are included in or adsorbed onto the dried product. In addition, the gel-like voluminous product leads to extremely long filtration and centrifugation times, which are very disadvantageous from the procedural point of view.

In comparison, Form III according to the invention is obtained as a colorless solid substance which forms good crystals and can be filtered and centrifuged without difficulty. Adhering mother liquor can be removed without difficulty by washing the filter cake with a suitable solvent, so that a product of high purity is obtained.

Amorphous solids, and hygroscopic solids even more so, cannot be processed at all satisfactorily into pharmaceuticals as, for example, they have low bulk densities and poor flow properties. Moreover, special operating techniques and devices are necessary for the handling of hygroscopic solids, in order to obtain reproducible results, for example, relating to the content of active ingredients or the stability in the final medicament produced.

Form III of doxazosin mesylate according to the invention can be used therapeutically in the same way as the doxazosin base and its pharmaceutically acceptable acid addition salts, and as the doxazosin mesylate having unknown morphological properties which is available on the market. The main areas of indication of the present Form III are the treatment of high blood pressure and the treatment of benign prostate hyperplasia.

The invention therefore further provides a pharmaceutical composition or medicament which, in addition to one or more conventional auxiliary substances and/or carriers, comprises Form III of doxazosin mesylate.

Thus, Form III of doxazosin mesylate according to the invention can be formulated into the conventional forms of administration, including peroral and parenteral forms of administration. Tablets or capsules are preferred formulations. They can be produced by conventional mixing processes and with the use of conventional auxiliary substances and carriers, as well as binders, disintegrants, flavorings and the like. The dose corresponds to that of the known forms of doxazosin salts.

In order to further illustrate the present invention and the advantages thereof, the following specific examples are given, it being understood that same are intended only as illustrative and in nowise limitative.

EXAMPLE 1

Production of Form III of Doxazosin Mesylate According to the Invention

In a 1 liter three-neck flask, 200 g doxazosin base are dissolved in 250 ml glacial acetic acid and 200 ml ethyl acetate by heating to 80° C. After addition of 23 ml methanesulfonic acid (70%), the hot solution is clarified through a layer of Supercel and the filter layer is washed with 30 ml of a hot mixture of glacial acetic acid and ethyl acetate (1:1). To the combined solutions, a further 23 ml methanesulfonic acid (70%) are added and the solution is stirred for one hour at 50° C. until crystallization occurs. After cooling to 10° C. and stirring for two hours, the precipitated solid is filtered by suction and washed with 200 ml ethyl acetate.

The solvent adduct that is still moist with ethyl acetate is then introduced into 1.0 l methanol and refluxed for 9 hours. After cooling to room temperature and filtration by suction, 240 g (99% th.) are obtained of a colorless solid that presents the X-ray diffraction spectrum of Form III shown in FIG. 1.

EXAMPLE 2

Production of Form III of Doxazosin Mesylate According to the Invention:

The doxazosin mesylate obtained in accordance with Example 1 that is moist with ethyl acetate is refluxed in ethanol amounting to three parts by volume for 3 hours.

After cooling to room temperature and filtration by suction, a colorless solid is again obtained in practically quantitative yield which according to its X-ray diffractogram is Form III of doxazosin mesylate and which also presents the DTA spectrum reproduced in FIG. 2.

While the invention has been described in terms of various preferred embodiments, the person skilled in the art will appreciate that various modifications, substitutions, omissions and changes can be made without departing from the spirit thereof. Accordingly, it is intended that the scope of the present invention be limited solely by the scope of the following claims, including equivalents thereof.

What is claimed is:

1. The polymorphic form of 1-(4-amino-6,7-dimethoxy-2-quinazolinyl)-4-[(2,3-dihydro-1,4-benzodioxin-2-yl) carbonyl]piperazine monomethanesulfonate which is crystalline and anhydrous and is characterized by an X-ray powder diffraction pattern having reflex positions of high and medium intensity at 8.49°, 11.72°, 16.03°, 18.29°, 21.03°, 22.87° and 25.02°.

2. A process for preparing the polymorphic form of 1-(4-amino-6,7-dimethoxy-2-quinazolinyl)-4-[(2,3-dihydro-1,4-benzodioxin-2-yl)carbonyl]piperazine monomethanesulfonate which is crystalline and anhydrous and is characterized by an X-ray powder diffraction pattern having reflex positions of high and medium intensity at 8.49°, 11.72°, 16.03°, 18.29°, 21.03°, 22.87° and 25.02°, said process comprising:

(1) reacting the base 1-(4-amino-6,7-dimethoxy-2-quinazolinyl)-4-[(2,3-dihydro-1,4-benzodioxin-2-yl) carbonyl]piperazine with acetic acid to afford 1-(4-amino-6,7-dimethoxy-2-quinazolinyl)-4-[(2,3-dihydro-1,4-benzodioxin-2-yl)carbonyl]piperazine acetate, optionally in an organic solvent;

(2) clarifying the solution obtained in stage (1) in the hot state and mixing it with methanesulfonic acid;

(3) stirring the solution obtained in stage (2) at a temperature of from about 30° C. up to the reflux temperature of the solvent to achieve substantially complete crystallization, and recovering the solvent adduct thus obtained by filtration;

(4) introducing the moist solvent adduct into a lower alkanol and boiling at the reflux temperature for between about 10 minutes and about 12 hours; and (5) cooling the solution obtained in stage (4) to room temperature and recovering by filtration the crystals of the desired polymorphic form of 1-(4-amino-6,7-dimethoxy-2-quinazolinyl)-4-[(2,3-dihydro-1,4-benzodioxin-2-yl)carbonyl]piperazine monomethanesulfonate which precipitate.

3. A pharmaceutical composition comprising, in solid dosage form:

(a) an effective $\alpha_1$-receptor blocking amount of 1-(4-amino-6,7-dimethoxy-2-quinazolinyl)-4-[(2,3-dihydro-1,4-benzodioxin-2-yl)carbonyl]piperazine monomethanesulfonate which is crystalline and anhydrous and is characterized by an X-ray powder diffraction pattern having reflex positions of high and medium intensity at 8.49°, 11.72°, 16.03°, 18.29°, 21.03°, 22.87° and 25.02°; and (b) a non-toxic, pharmaceutically acceptable carrier therefor.

4. A composition according to claim 3, in tablet or capsule form.

5. A pharmaceutical composition comprising, in solid dosage form:

(a) an effective antihypertensive amount of the polymorphic form of 1-(4-amino-6,7-dimethoxy-2-quinazolinyl)-4-[(2,3-dihydro-1,4-benzodioxin-2-yl) carbonyl]piperazine monomethanesulfonate which is crystalline and anhydrous and is characterized by an X-ray powder diffraction pattern having reflex positions of high and medium intensity at 8.49°, 11.72°, 16.03°, 18.29°, 21.03°, 22.87° and 25.02°; and (b) a non-toxic, pharmaceutically acceptable carrier therefor.

6. A composition according to claim 5, in tablet or capsule form.

7. A pharmaceutical composition comprising, in solid dosage form:

(a) an amount of the polymorphic form of 1-(4-amino-6,7-dimethoxy-2-quinazolinyl)-4-[(2,3-dihydro-1,4-benzodioxin-2-yl)carbonyl]piperazine monomethanesulfonate which is crystalline and anhydrous and is characterized by an X-ray powder diffraction pattern having reflex positions of high and medium intensity at 8.49°, 11.72°, 16.03°, 18.29°, 21.03°, 22.87° and 25.02°, which is effective against benign prostate hyperplasia; and (b) a non-toxic, pharmaceutically acceptable carrier therefor.

8. A composition according to claim 7, in tablet or capsule form.

9. A method for the treatment of high blood pressure in a warm-blooded animal in need of same, said method comprising administering to said animal an effective antihypertensive amount of the polymorphic form of 1-(4-amino-6,7-dimethoxy-2-quinazolinyl)-4-[(2,3-dihydro-1,4-benzodioxin-2-yl)carbonyl]piperazine monomethanesulfonate which is crystalline and anhydrous and is characterized by an X-ray powder diffraction pattern having reflex positions of high and medium intensity at 8.49°, 11.72°, 16.03°, 18.29°, 21.03°, 22.87° and 25.02°.

10. A method for the treatment of benign prostate hyperplasia in a warm-blooded animal in need of same, said method comprising administering to said animal an amount of the polymorphic form of 1-(4-amino-6,7-dimethoxy-2-quinazolinyl)-4-[(2,3-dihydro-1,4-benzodioxin-2-yl) carbonyl]piperazine monomethanesulfonate which is crystalline and anhydrous and is characterized by an X-ray powder diffraction pattern having reflex positions of high and medium intensity at 8.49°, 11.72°, 16.03°, 18.29°, 21.03°, 22.87° and 25.02°, which is effective against benign prostate hyperplasia.

11. A process according to claim 2, wherein stage (1) is conducted in an organic solvent.

12. A process according to claim 11, wherein the organic solvent is a lower alkyl alcohol or ester.

13. A process according to claim 12, wherein the lower alkyl alcohol or ester is ethyl acetate.

14. A process according to claim 2, wherein the ratio of doxazosin base to acetic acid in stage (1) is between about 1:2 and about 1:5.

15. A process according to claim 14, wherein the ratio of doxazosin base to acetic acid in stage (1) is between about 1:2 and about 1:3.

16. A process according to claim 2, wherein the reaction temperature in stage (1) is between about 40° C. and about 100° C.

17. A process according to claim 2, wherein the methanesulfonic acid introduced in stage (2) is employed in an approximately equimolar quantity relative to the doxazosin acetate.

18. A process according to claim 2, wherein the lower alcohol employed in stage (4) is methanol.

19. A composition according to claim 3, formulated for peroral administration.

20. A composition according to claim 5, formulated for peroral administration.

21. A composition according to claim 7, formulated for peroral administration.

* * * * *